(12) United States Patent
Kataoka et al.

(10) Patent No.: US 8,012,463 B2
(45) Date of Patent: Sep. 6, 2011

(54) COORDINATION COMPLEX OF DIAMINOCYCLOHEXANEPLATINUM(II) WITH BLOCK COPOLYMER CONTAINING POLY(CARBOXYLIC ACID) SEGMENT AND ANTITUMOR AGENT COMPRISING THE SAME

(75) Inventors: Kazunori Kataoka, Tokyo (JP); Nobuhiro Nishiyama, Tokyo (JP); Horacio Cabral, Tokyo (JP); Soichiro Okazaki, Fujieda (JP)

(73) Assignee: Toudai TLO, Ltd., Tokyo (JP)

( * ) Notice: Subject to any disclaimer, the term of this patent is extended or adjusted under 35 U.S.C. 154(b) by 1261 days.

(21) Appl. No.: 10/581,914

(22) PCT Filed: Dec. 8, 2004

(86) PCT No.: PCT/JP2004/018679

§ 371 (c)(1),
(2), (4) Date: Jun. 7, 2006

(87) PCT Pub. No.: WO2005/056641

PCT Pub. Date: Jun. 23, 2005

(65) Prior Publication Data

US 2007/0148125 A1    Jun. 28, 2007

(30) Foreign Application Priority Data

Dec. 10, 2003   (JP) ................................. 2003-412315

(51) Int. Cl.
*A61K 31/74* (2006.01)
(52) U.S. Cl. ................................... 424/78.17
(58) Field of Classification Search .................. None
See application file for complete search history.

(56) References Cited

U.S. PATENT DOCUMENTS

| | | | |
|---|---|---|---|
| 4,115,418 A | 9/1978 | Gale et al. | |
| 4,200,583 A | 4/1980 | Kidani et al. | |
| 4,452,812 A | 6/1984 | Macquet | |
| 4,485,093 A | 11/1984 | Runge | |
| 4,931,553 A | 6/1990 | Gill et al. | |
| 5,087,616 A | 2/1992 | Myers et al. | |
| 5,693,751 A | 12/1997 | Sakurai et al. | |
| 7,125,546 B2 | 10/2006 | Kataoka et al. | |
| 2003/0170201 A1* | 9/2003 | Kataoka et al. | 424/78.27 |
| 2003/0171430 A1* | 9/2003 | Kishimoto et al. | 514/492 |

FOREIGN PATENT DOCUMENTS

| | | |
|---|---|---|
| JP | 57-2296 | 1/1982 |
| JP | 5-301884 | 11/1993 |
| JP | 6-271593 | 9/1994 |
| JP | 6-329692 | 11/1994 |
| WO | PCT/FR97/00419 | 3/1997 |
| WO | 02/16376 A1 | 2/2002 |
| WO | 02/26241 A1 | 4/2002 |
| WO | 03/017923 A2 | 3/2003 |

OTHER PUBLICATIONS

Nobuhiro Nishiyama et al. "*Preparation and Characterization of Self-Assembled Polymer—Metal Complex Micelle from cis-Dichlorodiammineplatinum (II) and Poly(ethylene glycol) —Poly(αβ-aspartic acid) Block Copolymer in an Aqueous Medium*", Langmuir 1999, 15 (2), pp. 377-383.

Muenchen, H. J. et al., Anticancer Research, vol. 18, No. 4A, pp. 2631 to 2636 (1998).

Filipova-Voprsalova, M. et al., Journal of Controlled Release, vol. 17, No. 1, pp. 89 to 97 (1991).

Supplementary European Search Report issued May 28, 2009 in counterpart European Application No. 04807038.

Masahide Noji et al., "Synthesis of Pt(II) Complexes Containing D-Glucuronate, D-Gluconate, or Their Acetyl Derivatives and Evaluation of Antitumor Activity against Murine Leukemia L1210", Chemical and Pharmaceutical Bulletin, Pharmaceutical Society of Japan, Tokyo, vol. 36, No. 9, Sep. 25, 1988, pp. 3439-3446, XP009116263, ISSN: 0009-2363.

Muenchen, H. J. et al., Enhanced Immune System Activation after Treatment with Novel Antineoplastic Platinum Agents, Anticancer Research, vol. 18, No. 4A, pp. 2631-2636 (1998).

Filipová-Vopršálová, M. et al., Biodistribution of trans-1,2-diaminocyclohexane-trimellitatoplatinum (II) attached to macromolecular carriers I. Poly (hydroxyethyl-D,L-asparagine) carrier, Journal of Controlled Release, vol. 17, No. 1, pp. 89-87 (1991).

Rixe, O. et al., Oxaliplatin, Tetraplatin, Cisplatin, and Carboplatin: Spectrum of Activity in Drug-Resistant Cell Lines and in the Cell Lines of the National Cancer Institute's Anticancer Drug Screen Panel, Biochemical Pharmacology, vol. 52, pp. 1855-1865 (1996).

Misset, J. L. et al., Oxaliplatin Clinical Activity: A Review, Critical Reviews in Oncology/Hematology vol. 35, pp. 75-93 (2000).

Raymond E. et al., Cellular and Molecular Pharmacology of Oxaliplatin, Molecular Cancer Therapeutics, vol. 1, pp. 227-235 (2002).

Perez-Soler R. et al., Lipophilic Platinum Complexes Entrapped in Liposomes: Improved Stability and Preserved Antitumor Activity with Complexes Containing Linear Alkyl Carboxylato Leaving Groups, Cancer Chemotherapy and Pharmacology, vol. 33, pp. 378-384 (1994).

Kidani Y. et al., Antitumor Activity of 1,2-Diaminocyclohexane-Platinum Complexes against Sarcoma-180 Ascites Form, Journal of Medicinal Chemistry, vol. 21, No. 12, pp. 1315-1318 (1978).

Ohya Y. et al., Synthesis and cytotoxic activity of dextran carrying cis-dichloro(cyclohexane-*trans-l-*1,2-diamine)platinum (II) complex, J. Biomater. Sci. Polymer Edn, vol. 7 No. 12, pp. 1085-1096 (1996).

* cited by examiner

Primary Examiner — Michael G Hartley
Assistant Examiner — Paul Dickinson
(74) Attorney, Agent, or Firm — Wenderoth, Lind & Ponack, L.L.P.

(57) ABSTRACT

A coordinate complex of diaminocyclohexane platinum (II) with a block copolymer comprising a poly(ethylene glycol) segment and a poly(carboxylic acid) segment is provided. The complex can be effectively used in treatments for tumors, in particular malignant tumors.

11 Claims, 4 Drawing Sheets

Fig. 1

Drug encapsulated polymer micelle

COORDINATION COMPLEX OF DIAMINOCYCLOHEXANEPLATINUM(II) WITH BLOCK COPOLYMER CONTAINING POLY(CARBOXYLIC ACID) SEGMENT AND ANTITUMOR AGENT COMPRISING THE SAME

TECHNICAL FIELD

The present invention relates to a coordinate complex of diaminocyclohexane platinum (II) with poly(ethylene glycol)-poly(carboxylic acid) block copolymer, a method for producing the coordinate complex and an anti-tumor agent comprising the coordinate complex as an active ingredient.

BACKGROUND ART

Cisplatin which is a platinum compound, and carboplatin which is an analogue of cisplatin, (which corresponds to a compound in which dichloride that is a leaving group of cisplatin is substituted with 1,1-cyclobutane dicarboxylate) have early been used in clinical practice as it is effective particularly for cancer of generative organs. On the other hand, a cisplatin substituted derivative (dichlorodiaminocyclohexane platin (hereinafter referred to as "dichloro DACH platin)) in which two amino groups (or two amino ligands), a leaving group of cisplatin, are substituted with diaminocyclohexne (hereinafter referred to as "DACH"), is known to have good anti-tumor activities and provides a stable complex. However, because such DACH platinum complex is substantially insoluble in water, derivatives obtained by substituting the chloride leaving group (or ligands) with various anionic ligands have been proposed for improving their solubility. Great interest has been taken in some of such derivatives because they have an activity on, for example, cisplatin-resistant L-1210 leukemia cells. In particular, oxalate substituting DACH platinum complex presents good water-solubility as well as has a high therapeutic index, and has been provided for clinical trial as a third-generation anti-tumor platinum compound (see non-patent literatures 1, 2 and 3 below).

On the other hand, a liposome complex is also proposed as another type of the derivatives above which is produced by a carboxylate substituting DACH platinum complex is synthesized with using two molecules of higher fatty acids for increasing its fat-solubility contrary to the oxalate complex and is stably enclosed in the liposome (see non-patent literature 4 below).

In particular, for the oxalate substituting DACH platinum complex above [also referred to as Pt(oxalato)-(dach)], as described in the left-hand column of page 1856 of the non-patent literature 1, trans- and cis-isomer have been isolated as a geometric isomer and, for trans isomer, trans-1 and trans-d isomer are also isolated as two trans-optical isomers. Of these, Pt(oxalato)-(trans-1-dach) or cis-[(1R2R)-1,2-cyclohexanediamine-N,N']oxalato (2-)-O,O-platinum (II) (also referred to as oxaliplatin) has high water-solubility of 7.5 mg/mL (in 1.0M KCl aqueous solution at 37° C.). In addition, Pt(oxalato)-(dach) shows excellent $ED_{90}$ in experimental animals bearing ascites sarcoma 180. In contrast with such oxaliplatin, Pt(malonato)-(dach), which has dicarboxylic acids the same as oxalate, but has a different ligand, malonate, which is formed by adding one methylene group between two carboxyl groups, has been reported to show about 5 times or more $ED_{90}$ dose compared with Pt(oxalato)-(dach) (i.e. the drug efficacy shows one fifth or less) and half or less of therapeutic index of Pt(oxalato)-(cis-dach) (for example, see non-patent literature 5 below).

In addition to, so called low molecular prodrugs of Dichloro DACH platin as described above, high-molecular prodrugs using a polymer have been also proposed (see non-patent literature 6 below). In the non-patent literature 6, poly [N-2-hydroxypropyl]methacrylamide] (HPMA), poly(L-glutamic acid), poly(ethylene glycol)-block-poly(aspartic acid), oxidized dextran (OX-Dex) and the like are named as an example of polymers which can be used in such high-molecular prodrug systems, but only polymer complex of DACH platinum complex produced by using oxidized dextran or carboxymethyl-dextran (CM-Dex) is provided specifically. Furthermore, the non-patent literature 6 also describes that the OX-Dex complex has a more prolonged residual cytotoxic activity against experimental tumor cells in a serum-containing medium and shows stronger cytotoxicity compared with the CM-Dex complex. It is also suggested that such advantage of OX-Dex complex is due to the fact that DACH platinum complex will form a coordinate bond with OX-Dex stronger than with CM-Dex and steric hindrance level of the supporting polymer is also higher.

LIST OF LITERATURE

Non-patent literature 1: Oliver Rixe et al., Biochemical Pharmacology, Vol. 52, pp 1855-1865, 1996, in particular, summary section in page 1855 and left-hand column in page 1856, and page 1862 for typical derivative.

Non-patent literature 2: Jean Louis Misset et al., Critical Reviews in Oncology/Hematology 35 (2000) 75-93

Non-patent literature 3: Eric Raymond et al., Molecular Cancer Theapeutics Vol. 1, 227-235, 2002

Non-patent literature 4: Roman Perez-Soler et al., Cancer Chemotherapy and Pharmacology 33 (1994) 378-384

Non-patent literature 5: Yoshinori Kidani et al., American Chemical Society, vol. 21, 1315-1318, 1978, in particular page 1317, Tables III and IV Non-patent literature 6: Y Ohya et al., J. Biomater. Sci. Polymer Edn. Vol. 7, No. 12, pp. 1085-1096 (1996).

DISCLOSURE OF THE INVENTION

It has been suggested that oxaliplatin, as an anti-tumor platinum compound, has significantly improved water-solubility compared with Dichloro DACH platin, high efficacy and high therapeutic index, and can be used safely as an anti-tumor compound. However, it will be contributable to advancement of cancer chemotherapy if one can provide an anti-tumor platinum compound which can be used more safely than oxaliplatin.

Some of the inventors of the present invention had found previously that a coordinate complex of cisplatin with a block copolymer having a segment of poly(ethylene glycol) chain and a segment of poly(glutamic acid) (also referred to as "cisplatin encapsulated polymer micelle") makes external elimination of cisplatin significantly slowly compared with cisplatin itself (or increases half-life of the drug in blood), has good anti-tumor activity and reduced toxicity, and they had filed a patent application (see International Publication No.: WO 02/26241A1).

On the other hand, it is known that among DACH platinum complex, Pt(malonato)-(dach) complex, which carry a malonate of which carboxyl groups are separated by one methylene group, is inferior to Pt(oxalato)-(dach) complex, which carry oxalate as an anionic leaving group or ligand, in anti-tumor effect and therapeutic index. Furthermore, the inventors do not know any literature suggesting that such polymer complex have been provided for clinical trials.

Although such background is existing, the present inventors had attempted to synthesize a coordinate complex of DACH platinum complex with a block copolymer having a segment of poly(ethylene glycol) chain and a segment of poly(glutamic acid) chain or poly(aspartic acid) chain (also referred to as "DACH platinum complex encapsulated micelle").

As a result, it was unexpectedly confirmed that DACH platinum complex encapsulated micelle has increased anti-tumor effect and has attained far longer blood half-life than oxaliplatin, and it maintains stably polymer-micelle structure for very long period in the similar physiological condition, 10 mM phosphate buffered saline (PBS), although two carboxylates (or carboxyl anion), anionic leaving group in its ligand (the copolymer) are far apart from each other compared with that of oxalate, or being random. It was also confirmed that a growth inhibiting activity ($IC_{50}$) of DACH platinum complex encapsulated micelle is much higher than that of cisplatin encapsulated polymer micelle when colon cancer C-26 cells are exposed to these drugs for long period (48 and 72 hours). In addition, it was also found that some block copolymers, of which repeating unit having a carboxyl group at the side chain is different from that of glutamic acid, may have effects comparable to that of DACH platinum complex encapsulated micelle in some cases.

Furthermore, it was also confirmed that combined use of such DACH platinum complex encapsulated micelle and cisplatin encapsulated polymer micelle shows additive or synergic anti-tumor effect.

Thus, the present invention provides a coordinate complex of diaminocyclohexane platinum (II) with a block copolymer containing a structure of general formula (A):

PEG-block-poly(carbo)　　　　　　　　　　　(A)

(wherein PEG represents a poly(ethylene glycol) segment and carbo represents a repeating unit having a carboxyl group at its side chain) and provides a coordinate complex wherein the diaminocyclohexane platinum (II) is immobilized with the block copolymer via bonding of the carboxyl group of the carbo and the platinum.

A method for producing such coordinate complex and anti-tumor compositions comprising an anti-tumor effective amount of said coordinate complex and pharmaceutically acceptable carriers are also provided. A tumor-treatment method comprising an administration of an effective amount of such diaminocyclohexane platinum (II) complex to patients (mammal, especially human) requiring it is also provided as one embodiment of the present invention. As one mode of said anti-tumor composition and said tumor treatment method, an embodiment of the invention in which cisplatin encapsulated polymer micelle described in WO 02/26241A1 above (or complex of copolymer with cisplatin) is further combined for use is also provided.

Such coordinate complexes according to the present invention not only have useful characteristics superior to that of oxaliplatin, which is said to be the best anti-tumor drug among DACH platinum complexes, but also show so excellent stability under physiological condition (in body fluid etc.) that one can not expect it from cisplatin encapsulated polymer micelle previously developed by some of the present inventors, and they have also significantly good anti-tumor activities. In addition, they have superior accumulating specificity for tumor incomparable with cisplatin though its depositing specificity for liver is approximately same as that of free cisplatin (or cisplatin itself). Therefore, according to the present invention, it is possible to provide discriminating type of derivative of DACH platinum complexes, for examples, which can be used extremely safely and have increased anti-tumor activity compared with any known anti-tumor platinum compounds being known to have high level of toxicity usually.

DETAILED DESCRIPTION OF THE INVENTION

Figure 1:
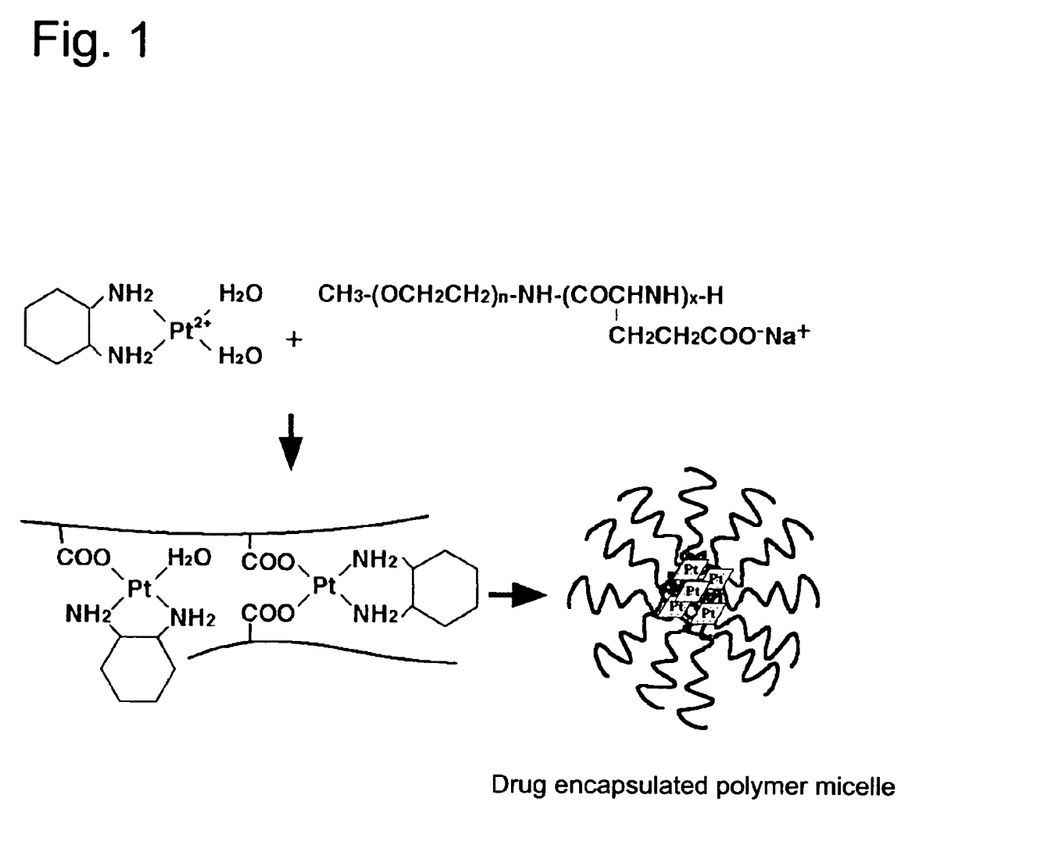
FIG. 1 is a schematic diagram of a coordinate complex and polymer micelle according to the present invention.

In coordinate complexes according to the present invention, a leaving group (or a ligand) of Dichloro DACH platin, chloride may be substituted with at least one carboxylate in one or two or more repeating units having a carboxyl group at the side chain of the block copolymer, and other leaving groups may be made aquatic (this means the state in which water molecule is coordinated with a platinum ion via an isolated electron-pair of oxygen atom). If two of the chlorides mentioned above are substituted with two carboxylates, said two carboxylates may be derived from those existing adjacently or far from each other in a single polymer molecule or multiple molecules. Though not limited to them, the structural formula of the coordinate complex and conceptual scheme of DACH platinum complex encapsulated micelle formed by those coordinate complexes in aqueous medium are shown in FIG. 1.

As described in non-patent literature 1 or 4, the DACH platinum complex portion can be various kinds of isomers, and the complex can be either a single kind of isomer or a mixture of various kinds of isomers, provided that they are suitable for the purpose of the invention.

On the contrary, although a block copolymer used for substituting the leaving group described above may be theoretically any block copolymers provided that they comprise a hydrophilic polymer segment and a poly(carboxylic acid) segment, and carboxylate (or carboxyl anion) of the poly(carboxylic acid) segment can bind to platinum (or platinum ion) in DACH platinum complex (so called coordinate bond), those which will be described later are preferable. Furthermore, it is preferred that such copolymer can form polymer-micelle consisting of a shell which form outer layer consisting of hydrophilic polymer segment and a core which form inner or center layer consisting of DACH platinum complex immobilized with poly(carboxylic acid) in aqueous solvent.

However, more specifically, it may include a block copolymer of the general formula (A) shown below which comprises a poly(ethylene glycol) chain or a poly(ethylene oxide) chain segment as the hydrophilic polymer segment.

PEG-block-poly(carbo)　　　　　　　　　　　(A)

wherein PEG represents a poly(ethylene glycol) segment and carbo represents a repeating unit having a carboxyl group at its side chain. The poly(carbo) can be derived from a polymer chain selected from the group consisting of poly(glutamic acid), poly(aspartic acid), poly(acrylic acid) and poly(methacrylic acid).

More preferable block copolymer for the purpose of the invention includes copolymers of the general formula (1) or (2) or a salt thereof

(1)

-continued (2)

wherein $R^1$ represents a hydrogen atom or an unsubstituted or substituted linear or branched $C_1$-$C_{12}$ alkyl group, $L^1$ and $L^2$ represent a linkage group, $R^2$ represents a methylene group or ethylene group, $R^3$ represents a hydrogen atom, a protecting group of amino group, a hydrophobic group or a polymerization group, $R^4$ represents a hydroxyl group or an initiator residue, $R^5$ represents independently a hydrogen atom or an alkali metal ion or a protecting group of carboxyl group, m represents an integer of 5 to 20,000, n represents an integer of 2 to 5,000, and x represents an integer of 0 to 5,000, with the proviso that x is not larger than n, and a hydrogen atom or alkali metal ion accounts for 50% or more, preferably 85% or more, more preferably 95% or more and particular preferably, substantially 100% of $R^5$'s the number of which is the sum of n-x and x.

In view of the object of the present invention, far more preferable block copolymer includes the one represented by the following general formula (1-a) or (2-a), or salts thereof.

wherein $R^1$ represents a hydrogen atom, an unsubstituted or substituted linear or branched $C_1$-$C_{12}$ alkyl group, $L^1$ and $L^2$ represent a linkage group, $R^3$ represents a hydrogen atom, a protecting group of amino group, a hydrophobic group or polymerization group, $R^4$ represents a hydroxyl group or an initiator residue, $R^5$ each represent independently a hydrogen atom or an alkali metal ion or a protecting group of carboxyl group, m represents an integer of 5 to 20,000 and n represents an integer of 2 to 5,000, with the proviso that a hydrogen atom or alkali metal ion accounts for 50% or more, preferably 85% or more, more preferably 95% or more, and particularly preferably substantially 100% of $R^5$'s the number of which is n.

Definition of each group or portion in the general formulas should be interpreted as that having standard meaning or content recognized by those skilled in the art. Specific examples thereof will be given below, but they are not limited to them.

For $R^1$, an unsubstituted or substituted, linear or branched $C_1$-$C_{12}$ alkyl group includes methyl, ethyl, n-propyl, iso-propyl, n-butyl, sec-butyl, tert-butyl, n-pentyl, n-hexyl, decyl, undecyl and the like. In case of substituted one, substituent includes an acetalized formyl group, cyano group, formyl group, carboxyl group, amino group, $C_1$-$C_6$ alcoxycarbonyl group, $C_2$-$C_7$ acylamide group, the same or different tri-$C_1$-$C_6$ alkylsiloxy group, siloxy group, or silylamino group. In the case where the substituent is an acetalized formyl group, it can be converted to other substituent formyl group (—CHO; or aldehyde group) by hydrolyzing it under mild acidic condition. Such formyl groups, or carboxyl groups or amino groups mentioned above can be allowed to be generated by deprotecting or converting a group or a part in the corresponding protected form after the coordinate complex of the present invention is prepared, for example, followed by, if necessary, covalent bonding a suitable antibody or a fragment having its specific binding property ((F(ab7)2, F(ab), or folic acid, etc.), and they can be utilized to impart target directivity to the coordinate complex. PEG segment having such functional groups at one terminal can be conveniently produced according to a manufacturing method for PEG segment of block copolymer described in, for example, WO 96/32434, WO 96/33233, or WO97/06202.

PEG segment and poly(carbo) segment thus produced can take any mode of linking depending on manufacturing method for the block copolymer of general formula (A), (1), (2), (1-a) or (2-a), and any linking mode can be acceptable provided that they meet the purpose of the invention. Although the manufacturing method is not restricted particularly, methods for producing complex of general formula (1), (2), (1-a) or (2-a) include the following: using PEG derivative having an amino group at its terminal, N-carboxylic acid anhydride (NCA) of β-benzyl-L-aspartate and/or γ-benzyl-L-glutamate is polymerized at the amino-terminal of PEG derivative to synthesize a block copolymer, followed by converting the side chain benzyl group to other ester group, or hydrolyzing partially or completely to obtain the desired block copolymer. In this case, the structure of the copolymer is the one represented by the formula (1) or (1-a), and the linking group $L^1$ will have a structure derived from the terminal structure of PEG segment used, but it preferably represents —$(CH_2)_b$—NH (in which b represent an integer of 1 to 5).

Furthermore, the copolymer according to the present invention can be produced by a method in which prepared poly(carboxylic acid) or poly(amino acid or a derivative thereof) segment is synthesized and then they are bound to a preliminarily prepared PEG segment. In this case, the copolymer produced may have the same structure as the polymer produced by the method described above or the structure corresponding to the general formula (2) or (2-a) may be obtained, and while the linking group $L^2$ is not limited particularly, it preferably represents —$(CH_2)_c$—CO (in which c represent an integer of 1 to 5).

$R^5$ in the general formula (1), (2) (1-a) or (2-a) can be each independently a hydrogen atom or a protecting group of carboxyl group. The protecting group of carboxyl group is not limited, but it includes benzyl, benzhydryl or a $C_1$-$C_6$ alkyl group, and specific examples of alkyl group include methyl, ethyl, n-propyl, iso-propyl, n-butyl, sec-butyl, tert-butyl, n-pentyl and n-hexyl.

$R^3$ can be each independently a hydrogen atom or a protecting group of amino group, for example, a benzyloxycarbonyl, t-butyloxycarbonyl, acetyl or trifluoroacetyl group and the like, and it can also be a hydrophobic group such as a benzylcarbonyl or benzhydrylcarbonyl group and the like, or polymerization group such as acryloyl or methacryloyl and the like.

$R^4$ can be each independently a protecting group of hydroxyl group or carboxyl group, for example, a benzyloxy, t-butyloxy or methoxy group, and the like, a hydrophobic group such as a benzyloxy or benzhydryloxy group and the like, or polymerization group such as an allyloxy or vinylphenylmethoxy group and the like. Such polymerization group forms a polymer micelle comprised of the coordinate complex of the present invention, followed by polymerization to make the structure of the polymer micelle harder. However it is not necessary in most cases for the inventive drug encapsulated polymer-micelle to be subjected to such polymerization because the inventive polymer-micelle often keeps its micelle structure during releasing the drug outside the micelle.

m and n each are an integer of 5 to 20,000, preferably 10 to 5,000, particularly preferably 40 to 500, and an integer of 2 to 5,000, more preferably 5 to 1,000, particularly preferably 10 to 200, respectively. Thus, a term "poly" is used as a concept including so-called "oligo" in the specification, although the term is conveniently used to express poly(ethylene glycol), poly(carboxylic acid) and the like.

In the case of a poly(amino acid or derivative thereof) segment, particularly poly(aspartic acid), x, which defines a composition rate of two repeating units, can be an integer of 0 to 5,000 (but not lager than n). In this case, the repeating unit can distribute randomly or in blocks.

For the coordinate complex according to the present invention, the equivalent ratio of platinum (Pt) of diaminocyclohexane platinum (II) to a carboxyl group (carboxyl anion) of the block copolymer (Pt/COO—) is preferably 0.05 or more, more preferably 0.1 or more, and particularly preferably 0.3 to 1.0 or 1.2. The upper limit of the ratio can be theoretically 2.0 for coordinate complex. However, in the case when the coordinate complex is used as an anti-tumor drug, it can include diaquo-diaminocyclohexane platinum (II) complex in addition to diaminocyclohexane platinum (II) forming a coordinate complex with the copolymer provided that it is suitable for the purpose of the invention. The coordinate complex according to the present invention, for example, as illustrated in FIG. 1, can conveniently be produced by binding diaquo-diaminocyclohexane platinum (II) complex (Diaquo DACH Platin) and a block copolymer comprising a structure of the following general formula (A) in an aqueous solvent under an equivalent ratio of Pt and a carboxyl group and the condition in which platinum (Pt) of Diaquo DACH Platin (II) can bind to a carboxyl anion of the block copolymer:

$$\text{PEG-block-poly(carbo)} \tag{A}$$

(wherein PEG represents a poly(ethylene glycol) segment and carbo represents repeating units having carboxyl groups at the side chain), and recovering coordinate complex thus produced with diaminocyclohexane platinum (II) and the copolymer. And Diaquo DACH Platin can be used for the complex-producing reaction in the form of aqueous solution which is obtained by reacting dichloro(1,2-diaminocyclohexane) platinum (II) with silver nitrate and removing silver chloride, by-product of the reaction. Dichloro(1,2-diaminocyclohexane) platinum (II) and Diaquo DACH Platin are known compounds (for example, see non-patent literature 5 or 2).

Although any reaction condition can be used provided that the desired coordinate complex can be obtained, it is preferable to select usage amounts of Diaquo DACH Platin and the block copolymer so that an equivalent ratio of Pt to carboxyl group will be 0.1 or more, preferably 0.3 or more, and 1 at the maximum, a concentration at which both reactants are solved or partially suspended, and a reaction temperature of 5 to 60° C. The aqueous solvent referred to herein means water (in particular deionized water) or various inorganic or organic buffers, or solvent which may contain a water-miscible organic solvent such as acetonitrile, dimethylformamide, ethanol and the like as much as they do not affect on the complex formation reaction. Since the coordinate complex produced is usually a polymer micelle solubilized in an aqueous solvent (generally having an average particle diameter of from 20 nm to 500 nm, measured by dynamic light scattering method), the polymer micelle can be recovered from the reaction mixture by ordinary methods for isolation and purification. Typical methods include ultrafiltration, diafiltration and dialysis method.

A DACH platin encapsulated polymer micelle solution thus isolated and purified can be sterilized directly and, if necessary, prepared as an injectable solution by adding known excipients suitable for injectable reagents, or as fine powder by concentrating and then, for example, lyophilizing the polymer micelle solution. The fine powder can be dissolved at considerably high concentration in an injectable solution, and the DACH platin encapsulated polymer micelle according to the present invention can be also prepared as a pharmaceutical preparation for bolus injection since it is much safer than oxaliplatin. Said fine powder may be mixed with pharmaceutically acceptable carriers and formulated into any dosage form suitable for various administration mode. Representative examples of such carrier are deionized water, aqueous solution buffered to a given pH, oligo- or polyethylene glycol, monosaccharide or oligosaccharide, sugar alcohol and the like. However, it is preferable to provide a composition formulated into any form suitable for parenteral administration, in particular intravenous or subcutaneous administration.

For example, for dosage used for intra venous administration, it is preferable to determine it by specialists considering results of a small-scale experiment based on experimental animals or volunteers and patients' conditions. However, dose may be, without limitation, normally 1.0 to 1000 mg/m$^2$ (patient's body surface area) once a day, and an appropriate dose may be selected depending on the administration schedule including 10 to 200 mg/m$^2$ (patient's body surface area) once a day for several continuous days followed by a pause period or 50 to 500 mg/m$^2$ (patient's body surface area) once a day one day followed by a pause of several days.

The coordinate complex of the invention has an anti-tumor activity spectrum similar to that of dichloro(1,2-diaminocyclohexne) platinum (II), Diaquo DACH Platin or oxaliplatin. Thus, the invention provides anti-tumor agents comprising the coordinate complex above as an active constituent.

According to the invention, tumor of interest may include anti-carcinoma, bladder cancer, renal pelvis/ureter tumor, prostate cancer, ovarian cancer, head-neck cancer, alveolar carcinoma, esophageal cancer, cervical cancer, neuroblastoma, stomach cancer and rectal cancer but it is not limited to them provided that DACH Platin encapsulated polymer micelle or complexes of DACH Platin and the copolymer according to the invention is effective.

DACH Platin encapsulated polymer micelle or the complex according to the invention may be used in combination with other anti-tumor agents or anticancer agents. Any anti tumor agent can be used provided that it does not result in adverse effect in the combined use, and it includes, for example, cytarabine, 5-FU, doxorubicin, taxsol, carboplatin, cisplatin. Particular preferred is a combination use with cisplatin encapsulated polymer micelle (or the complex of copolymer with cisplatin) described in WO 02/26241A1 above, and it includes specifically a combined use of a cisplatin coordinate complex, which consists of cisplatin as an anti-tumor active ingredient, and a block copolymer represented by the general formula (1-a) or (2-a):

(wherein $R^1$ represents a hydrogen atom, or an unsubstituted or substituted, linear or branched $C_1$-$C_{12}$ alkyl group, $L^1$ and $L^2$ represent a linkage group, $R^3$ represents a hydrogen atom, a protecting group of amino group, a hydrophobic group or a polymerization group, $R^4$ represents a hydroxyl group or an initiator residue, $R^5$ each represent independently a hydrogen atom or an alkali metal ion or a protecting group of carboxyl group, m represents an integer of 5 to 20,000 and n represents an integer of 2 to 5,000, with the proviso that the alkali metal ion accounts for 50% or more of $R^5$'s the number of which is n), or encapsulated polymer micelle thereof, and DACH Platin encapsulated polymer micelle or the complex of DACH Platin and the copolymer above. Although it is not limited to a specific combination ratio, the ratio of DACH Platin encapsulated polymer micelle (or a diaminocyclohexane platinum (II) coordinate complex) to said cisplatin coordinate complex is preferably 1/3 to 3/1, in particular 1/1 to 3/1, based on the platinum weight.

In these combined uses, two or more agents being combined may be administered to patients simultaneously or separately through the same or different administration route. The combination of DACH Platin encapsulated polymer micelle and said cisplatin coordinate complex may be formulated into a single preparation and used effectively.

BEST MODE FOR CARRYING OUT THE INVENTION

The present invention will be described more specifically by way of particular examples, but it is not intended to limit the present invention thereto.

Example 1

Production of the Polymer Micelle

The structural formula of the block copolymer used in this example is as follows:

(1.a.) 19 mg of dichloro(1,2-diaminocyclohexane) platinum (II)(dichloro-DACH Pt) was suspended in 10 ml of distilled water, and the suspension was mixed with 12.3 mg of silver nitrate (molar ratio of [$AgNO_3$]/[dichloro-DACH Pt]=1.5). The mixture was kept at a dark place at 25° C. for 24 hours. After the reaction, silver chloride was precipitated. Then, the reaction mixture was centrifuged at 3,000 rpm for 5 minutes to remove the precipitate of silver chloride. The thus obtained Diaquo DACH Pt containing supernatant was purified by filtration with a 0.22 μm pore-size filter.

(1.b.) 24.4 mg of the block copolymer represented by the structural formula given above (hereinafter referred to as PEG-P(Glu)12-35), in which m is such a value that a molecular weight of poly(ethylene glycol) segment becomes about 12,000 and n is about 35, was added to 10 ml of the purified supernatant obtained in (1.a.) (molar ratio of "Diaquo-DACH Pt"/[Glu]=1).

The solution thus obtained was stirred at 37° C. for 120 hours. The solution was loaded into a dialysis bag (molecular weight cut off (MWCO)=1000) and dialyzed against distilled water for 24 hours. Water outside the dialysis bag (membrane) was changed 30 minutes, 1 hour, 2 hours, 3 hours, 4 hours, 6 hours and 12 hours after starting the dialysis. The dialyzed solution was subjected to ultrafiltration with a filter (MWCO=100,000).

Example 2

Characteristics of the Polymer Micelle (2.a.) Stability in 10 mM PBS

Stability of the polymer micelle produced in Example 1 (hereinafter referred to as DACH Pt micelle) was compared with that of a cisplatin encapsulated polymer micelle (hereinafter referred to as CDDP micelle) produced according to the procedure of Example 1 of WO 02/26241A1 described above using the same block copolymer in (1.a.) above.

In brief, CDDP micelle was prepared as follows: Cisplatin (CDDP) was dissolved in water (5 mmol/l). Into this solution, the same copolymer as the one used in Example 1 above was dissolved ([CDDP]/[Glu in the co-polymer]=1.0) and incubated at 37° C. for 73 hours. The resulting solution was subjected and purified by repeating ultrafiltration (MWCO=100,000). Formation of polymer micelle was confirmed by measuring its dynamic light scattering (DLS).

A certain volume of the micelle solution was first lyophilized, and then the residue was weighed to determine the concentration of the micelle. DACHPt micelle solution and CDDP micelle solution were mixed with 10 mM PBS (pH 7.4) solution supplemented with 150 mM NaCl respectively to obtain 1.5 mg/ml of micelle concentrated solutions. Those solutions were kept in dark at 37° C. Samples were collected from both solutions and then they were measured by dynamic light scattering (SLS) method. Scattered light was measured at 25° C. and detected at an agree of 90°. Those solutions were purified by filtration with a 0.45 μm-filter.

Figure 2:
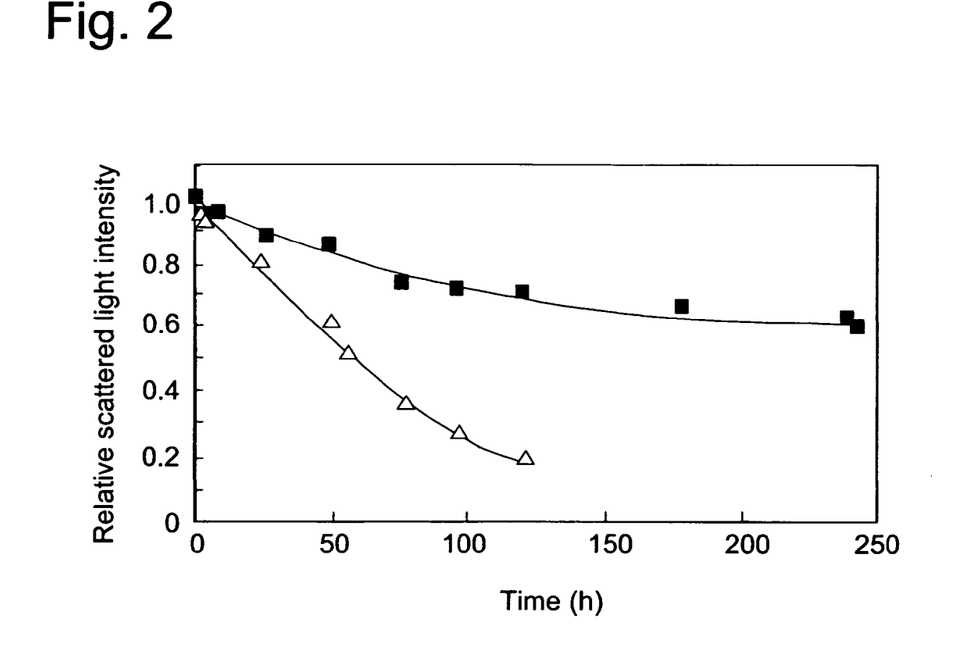
FIG. 2 is a graph showing change of relative scattering light intensity of DACH Pt micelle (closed square) and CDDP micelle (triangle).

Result of Stability Assay:

Change in relative intensity of scattering light, i.e. change in the intensity of scattering light from the initial intensity to the intensity at the specific time is shown in FIG. 2. From FIG. 2, it can be seen that CDDP micelle dissociated within about 50 hours but DACH Pt micelle was stable up to 250 hours.

(2.b.) Release of Platinum from Micelle

Release of platinum from DACH Pt micelle and CDDP micelle in 10 mM PBS (pH 7.4) added with 150 mM NaCl were evaluated by dialysis method (MWCO of the membrane=1,000) at various temperatures. Pretreatment of dichloro-DACH Pt with silver-nitrate was carried out in both dimethylformamide (DMF) and water, and then two kinds of DACH Pt micelles were prepared according to the method described in (1.B.). The outer solutions of dialysis bag were sampled at a specific interval and concentration of platinum was measured by an inductive plasma mass spectrometric device (ICP-MS).

Figure 3:
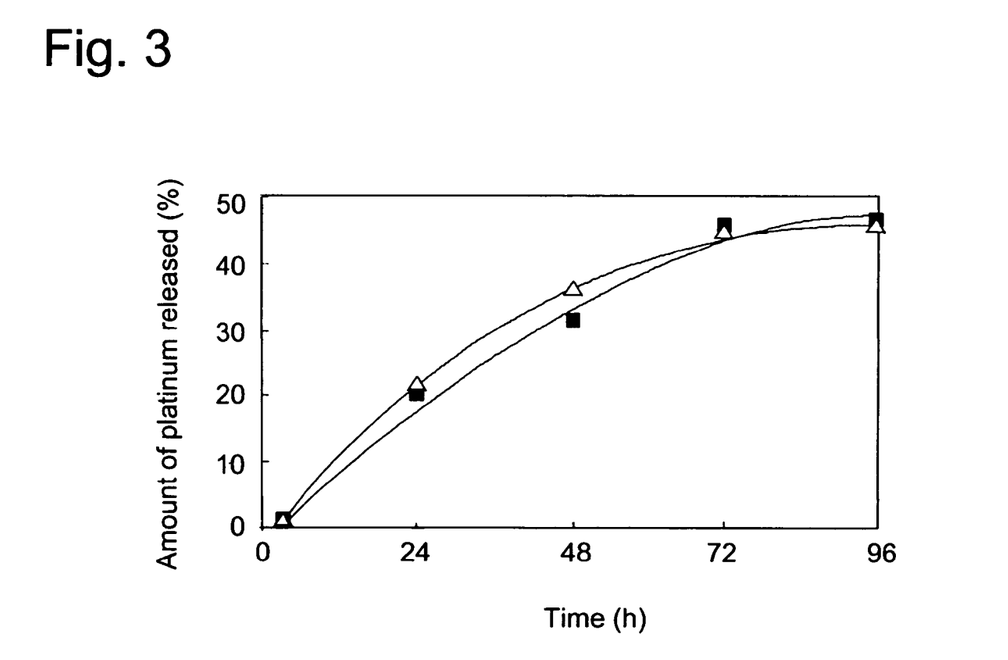
FIG. 3 is a graph showing releasing behavior of platinum from DACH Pt micelle (closed square) and CDDP micelle (triangle) in a 10 mM PBS solution (pH 7.4) added with 150 mM NaCl.

Result:

The result regarding the release is shown in FIG. 3. The platinums released from CDDP micelle and DACH Pt micelle pre-treated in DMF were similar. DACH Pt micelle pre-treated with water showed slightly higher release of platinum. DACH Pt micelle showed higher stability in 150 mM NaCl than CDDP micelle, but its releasing rate of platinum was similar to that of CDDP micelle.

(2.c.) Cytotoxicity In Vitro

Growth inhibiting activities of free CDDP, CDDP micelle, DACH Pt micelle, mixtures of DACH Pt micelle and CDDP micelle at various mixing ratios (1/3, 1/1 and 3/1) against mouse colon 26 (C-26) cell strain were evaluated with MTT method. 5,000 cells were cultured in a 96 well-multiplate supplied with 50 μl of RPMI 1640 medium containing 10% fetal bovine serum. The cells were exposed to drugs for 48 and 72 hours. MTT solution was added, and 150 μl of a solution containing 10 wt % of sodium dodecylsulfate (SDS) supplemented with 0.01M HCl was added after 6 hours. Viability of cells was then measured based on optical density at 570 nm of formazan produced after 24 hours. From these results, results of 50% inhibition concentrations ($IC_{50}$) determination are summarized in Table 1.

TABLE 1

| Culture time (Hour) | Free CDDP | CDDP Micelle | 0.25 DACHPt Micelle +0.75 CDDP Micelle | 0.5 DACHPt Micelle +0.5 CDDP Micelle | 0.75 DACHPt Micelle +0.25 CDDP Micelle | DACHPt Micelle |
|---|---|---|---|---|---|---|
| | | | $IC_{50}$ (μg/ml) | | | |
| 48 | 1.5 | 20.3 | 8 | 3.5 | 3 | 2.3 |
| 72 | 0.65 | 7.5 | 2 | 0.8 | 1.25 | 1.5 |

From the table, it can be seen that DACH Pt micelle has about 10 times higher cytotoxic activity (anti-tumor activity) than CDDP micelle. And combining these micelles enhances the cytotoxic activity.

(2.d.) In Vivo Distribution

Figure 4:
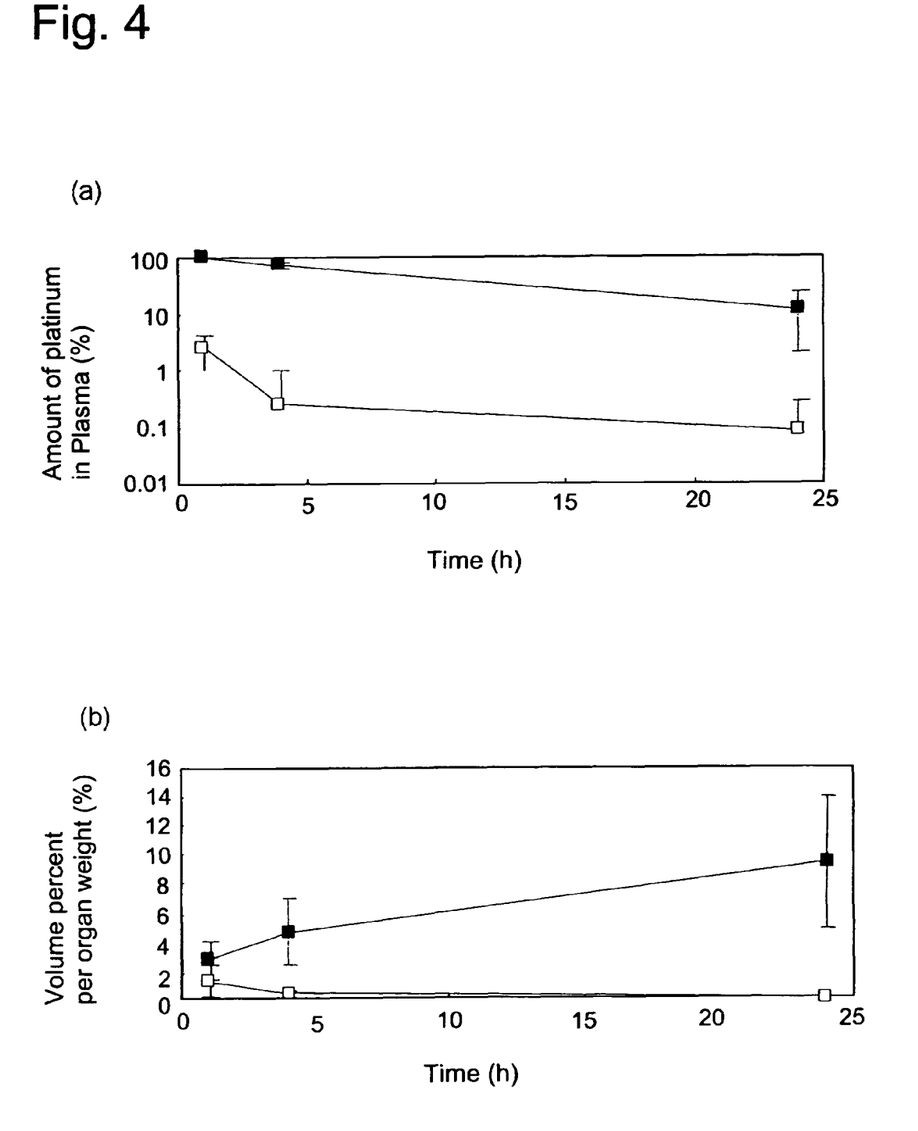
FIG. 4 is a graph showing accumulating-characteristic of the drug, DACH Pt micelle (closed square) and free-CDDP micelle (opened square) into plasma (a) and various organs (specifically tumor (b), kidney (c) and liver (d)).

Balb/c mice (n=3, male, 6 weeks, 20 to 25 g) were subcutaneously inoculated with C-26 ($1 \times 10^6$) cells via one right abdominal side of body. Free CDDP and DACH Pt micelles (100 μg of drug) were injected via caudal veins. On the 21st day after the inoculation, mice were sacrificed. At 1, 4 and 24 hours, tumor, liver, kidney were excised and blood was collected at the same time, and then blood was heparinized. Plasma was separated from blood by centrifugation, and then dissolved in warm nitric acid. The organs were weighed, and then they were dissolved in warm nitric acid. The solution was dried. The amount of platinum was measured by ICP-MS immediately after the addition of hydrochloric acid. The result is shown in FIG. 4. From the result, it is understood that DACH Pt micelle retains in blood for long period and accumulated effectively into solid cancer without no specific accumulation in normal tissues.

INDUSTRIAL APPLICABILITY

The coordinate complex of the present invention can be use safely in human tumor chemotherapy, and it can also be utilized in medical industry, pharmaceutical industry and the like because of its strong anti-tumor activity.

The invention claimed is:

1. A coordinate complex in the form of a polymer micelle, said polymer micelle encapsulating a complex of diaminocyclohexane platinum (II) and a block copolymer comprising a structure of the general formula (A):

PEG-block-poly(carbo) (A)

wherein PEG represents a poly(ethylene glycol) chain segment and poly(carbo) represents a polymer chain segment having a carboxyl group and selected from the group consisting of poly(glutamic acid) chain segment and poly(aspartic acid) chain segment;

wherein diaminocyclohexane platinum (II) is immobilized with the block copolymer via bonding between carboxyl anion of poly(carbo) and the platinum and wherein copolymer is represented by the following general formula (1) or (2), or a salt thereof:

-continued wherein
R¹ represents a hydrogen atom or an unsubstituted or substituted linear or branched $C_{1-12}$ alkyl group;
L¹ represents —$(CH_2)_b$—NH— wherein b represents an integer of 1 to 5;
L² represents —$(CH_2)_c$—CO— wherein c represents an integer of 1 to 5;
R² represents a methylene group or ethylene group;
R³ respectively and independently represents an atom or a group selected from the group consisting of a hydrogen atom, a benzyl oxycarbonyl group, a t-butyl oxycarbonyl group, an acetyl group, a trifluoroacetyl group, a benzyl carbonyl group, a benzhydryl carbonyl group, an acryloyl group and methacryloyl group;
R⁴ respectively and independently represents a group selected from the group consisting of a hydroxyl group, a benzyloxy group, a t-butyloxy group, a methoxy group, a benzhydryloxy group, an allyloxy group and a vinyl phenyloxy group;
R⁵ respectively and independently represents a hydrogen atom, an alkali metal ion, a group selected from the group consisting of a benzyl group, a benzhydryl group and a $C_{1-6}$ alkyl group;
m represents an integer of 5 to 20,000;
n represents an integer of 2 to 5,000; and
x represents an integer of 0 to 5,000, with the proviso that x is not larger than n, and that hydrogen atoms or alkali metal ions account for 50% or more of R⁵'s the number of which is the sum of n-x and x wherein the equivalent ratio of platinum (Pt) of diaminocyclohexane platinum (II) to a carboxyl group of the block copolymer (Pt/COO⁻) is from 0.3 to 1.

2. The coordinate complex according to claim 1, wherein the structure of the block copolymers is represented by the general formula (1-a) or (2-a):

wherein
R¹ represents a hydrogen atom or an unsubstituted or substituted linear or branched $C_{1-12}$ alkyl group;
L¹ represents —$(CH_2)_b$—NH— wherein b represents an integer of 1 to 5;
L² represents —$(CH_2)_c$—CO— wherein c represents an integer of 1 to 5;
R³ respectively and independently represents an atom or a group selected from the group consisting of a hydrogen atom, a benzyl oxycarbonyl group, a t-butyl oxycarbonyl group, an acetyl group, a trifluoroacetyl group, a benzyl carbonyl group, a benzhydryl carbonyl group, an acryloyl group and a methacryloyl group;
R⁴ respectively and independently represents a group selected from the group consisting of a hydroxyl group, a benzyloxy group, a t-butyloxy group, a methoxy group, a benzhydryloxy group, an allyloxy group and a vinyl phenyl methoxy group;
R⁵ respectively and independently represents a hydrogen atom, an alkali metal ion, a group selected from the group consisting of a benzyl group, a benzhydryl group and a $C_{1-6}$ alkyl group;
m represents an integer of 5 to 20,000; and
n represents an integer of 2 to 5,000, with the proviso that hydrogen atoms or alkali metal ions account for 50% or more of R⁵'s the number of which is n.

3. The coordinate complex according to claim 2, wherein all of R⁵'s in general formula (1-a) or (2-a) represent a hydrogen ion or an alkali metal ion.

4. The coordinate complex according to claim 1, wherein the polymer micelle has a core-shell structure in which the poly(ethylene glycol) segment forms the shell and the polymer chain segment selected from the group consisting of a poly(glutamic acid) chain segment and a poly(aspartic acid) chain segment forms the core.

5. A coordinate complex in the form of a polymer micelle, said polymer micelle comprises a complex of diaminocyclohexane platinum (II) and a block copolymer comprising a structure of the general formula (I-a) or (2-a):

wherein
R¹ represents a hydrogen atom or an unsubstituted or substituted linear or branched $C_{1-12}$ alkyl group;
L¹ represents —$(CH_2)_b$—NH— wherein b represents an integer of 1 to 5;
L² represents —$(CH_2)_c$—CO— wherein c represents an integer of 1 to 5;
R³ respectively and independently represents an atom or a group selected from the group consisting of a hydrogen atom, a benzyl oxycarbonyl group, a t-butyl oxycarbonyl group, an acetyl group, a trifluoroacetyl group, a benzyl carbonyl group, a benzhydryl carbonyl group, an acryloyl group and a methacryloyl group;
R⁴ respectively and independently represents a group selected from the group consisting of a hydroxyl group, a benzyloxy group, a t-butyloxy group, a methoxy group, a benzhydryloxy group, an allyloxy group and a vinyl phenyl methoxy group;
R⁵ respectively and independently represents a hydrogen atom, an alkali metal ion, a group selected from the group consisting of a benzyl group, a benzhydryl group and a $C_{1-6}$ alkyl group;
m represents an integer of 5 to 20,000;
n represents an integer of 2 to 5,000, with the proviso that hydrogen atoms or alkali metal ions account for 50% or more of $R^5$'s the number of which is n; wherein diaminocyclohexane platinum (II) is immobilized with the block copolymer via bonding between carboxyl anion of the block copolymer represented by the general formula (I-a) or (2-a) and the platinum, and the equivalent ratio of platinum (Pt) of diaminocyclohexane platinum (II) to a carboxyl group of the block copolymer (Pt/COO⁻) is from 0.3 to 1.

6. A method for producing the coordinate complex according to claim 1, comprising reacting diaquo diaminocyclohexane platinum (II) complex (Diaquo DACH Platin) with the block copolymer of the structure represented by the general formula (A):

$$\text{PEG-block-poly(carbo)} \tag{A}$$

in an aqueous solvent at the equivalent ratio of platinum(Pt) of Diaquo DACH Platin (II) to the carboxyl group of said block copolymer and the condition in which bond formation between said platinum and carboxyl anion of said block copolymer can be allowed, and recovering the coordinate complex thus obtained from said diaminocyclohexane platinum (II) and said block copolymer.

7. The production method according to claim 6, wherein Diaquo DACH Platin is present in an aqueous solution which is obtained by reacting dichloro(1,2-diaminocyclohexane) platinum (II) with silver nitrate in an aqueous solvent and removing by-produced silver chloride.

8. The production method according to claim 6, wherein the structure of the block copolymer is represented by the following general formula (1-a) or (2-a):

$$R^1O{-}(CH_2CH_2O)_m{-}L^1{-}(COCHNH)_n{-}R^3 \atop \underset{\underset{\underset{OR^5}{|}}{\underset{C=O}{|}}}{\underset{(CH_2)_2}{|}} \tag{1-a}$$

$$R^1O{-}(CH_2CH_2O)_m{-}L^2{-}(NHCHCO)_n{-}R^4 \atop \underset{\underset{\underset{OR^5}{|}}{\underset{C=O}{|}}}{\underset{(CH_2)_2}{|}} \tag{2-a}$$

wherein $R^1$ represents a hydrogen atom or an unsubstituted or substituted linear or branched $C_{1-12}$ alkyl group;

$L^1$ represents —$(CH_2)_b$—NH— wherein b represents an integer of 1 to 5;

$L^2$ represents —$(CH_2)_c$—CO— wherein c represents an integer of 1 to 5;

$R^3$ respectively and independently represents an atom or a group selected from the group consisting of a hydrogen atom, a benzyl oxycarbonyl group, a t-butyl oxycarbonyl group, an acetyl group, a trifluoroacetyl group, a benzyl carbonyl group, a benzhydryl carbonyl group, an acryloyl group and a methacryloyl group;

$R^4$ respectively and independently represents a group selected from the group consisting of a hydroxyl group, a benzyloxy group, a t-butyloxy group, a methoxy group, a benzhydryloxy group, an allyloxy group and a vinyl phenyl methoxy group;

$R^5$ respectively and independently represents a hydrogen atom, an alkali metal ion, a group selected from the group consisting of a benzyl group, a benzhydryl group and a $C_{1-6}$ alkyl group;

m represents an integer of 5 to 20,000;

n represents an integer of 2 to 5,000, with the proviso that hydrogen atoms or alkali metal ions account for 50% or more of $R^5$'s the number of which is n.

9. An anti-tumor composition comprising an anti-tumor effective amount of a coordinate complex in the form of a micelle and a pharmaceutically acceptable carrier, said coordinate complex comprising diaminocyclohexane platinum (II) and the block copolymer having the structure represented by the general formula (A):

$$\text{PEG-block-poly(carbo)} \tag{A}$$

wherein PEG represents a poly(ethylene glycol) chain segment and poly(carbo) represents a polymer chain segment having a carboxyl group and selected from the group consisting of poly(glutamic acid) chain segment and poly(aspartic acid) chain segment, wherein diaminocyclohexane platinum (II) is immobilized with the block copolymer via binding between carboxyl anion of poly(carbo) and the platinum, and wherein the block copolymer is represented by the following general formula (1) or (2), or salt thereof:

$$R^1O{-}(CH_2CH_2O)_m{-}L^1{-}(COCHNH)_{n-x}{-}(COR^2CHNH)_x{-}R^3 \atop \underset{\underset{\underset{OR^5}{|}}{\underset{C=O}{|}}}{\underset{R^2}{|}} \quad \underset{COOR^5}{|} \tag{1}$$

$$R^1O{-}(CH_2CH_2O)_m{-}L^2{-}(NHCHCO)_{n-x}{-}(NHCHR^2CO)_x{-}R^4 \atop \underset{\underset{\underset{OR^5}{|}}{\underset{C=O}{|}}}{\underset{R^2}{|}} \quad \underset{COOR^5}{|} \tag{2}$$

wherein $R^1$ represents a hydrogen atom or an unsubstituted or substituted liner or branched $C_{1-12}$ alkyl group;

$L^1$ represents —$(CH_2)_b$—NH— wherein b represents an integer of 1 to 5;

$L^2$ represents —$(CH_2)_c$—CO— wherein c represents an integer of 1 to 5;

$R^2$ represents a methylene group or ethylene group;

$R^3$ respectively and independently represents an atom or a group selected from the group consisting of a hydrogen atom, a benzyl oxycarbonyl group, a t-butyl oxycarbonyl group, an acetyl group, a trifluoroacetyl group, a benzyl carbonyl group, a benzhydryl carbonyl group, an acryloyl group and methacryloyl group;

$R^4$ respectively and independently represents a group selected from the group consisting of a hydroxyl group, a benzyloxy group, a t-butyloxy group, a methoxy group, a benzhydryloxy group, an allyloxy group and a vinyl phenyloxy group;

$R^5$ respectively and independently represents an atom or a group selected from the group consisting of a hydrogen atom, an alkali metal ion, a benzyl group, a benzhydryl group and a $C_{1-6}$ alkyl group;

m represents an integer of 5 to 20,000;

n represents an integer of 2 to 5,000; and x represents an integer of 0 to 5,000 with the proviso that x is not larger than n, and that hydrogen atoms or alkali metal ions account for 50% or more of $R^5$'s the number of which is the sum of n-x and x wherein the equivalent ratio of platinum (Pt) of diaminocyclohexane platinum (II) to a carboxyl group of the block copolymer (Pt/COO$^-$) is from 0.3 to 1.

10. The anti-tumor composition according to claim 9, further comprising a cisplatin coordinate complex as an anti-tumor active ingredient, said cisplatin coordinate complex consisting of cisplatin and the block copolymer represented by the general formula (I-a) or (2-a):

wherein $R^1$ represents a hydrogen atom or an unsubstituted or substituted linear or branched $C_{1-12}$ alkyl group;

$L^1$ represents —$(CH_2)_b$—NH— wherein b represents an integer of 1 to 5;

$L^2$ represents —$(CH_2)_c$—CO— wherein c represents an integer of 1 to 5;

$R^3$ respectively and independently represents an atom or a group selected from the group consisting of a hydrogen atom, a benzyl oxycarbonyl group, a t-butyl oxycarbonyl group, an acetyl group, a trifluoroacetyl group, a benzyl carbonyl group, a benzhydryl carbonyl group, an acryloyl group and a methacryloyl group;

$R^4$ respectively and independently represents a group selected from the group consisting of a hydroxyl group, a benzyloxy group, a t-butyloxy group, a methoxy group, a benzhydryloxy group, an allyloxy group and a vinyl phenyl methoxy group;

$R^5$ respectively and independently represents a hydrogen atom, an alkali metal ion, a group selected from the group consisting of a benzyl group, a benzhydryl group and a $C_{1-6}$ alkyl group; m represents an integer of 5 to 20,000;

n represents an integer of 2 to 5,000, with the proviso that hydrogen atoms or alkali metal ions account for 50% or more of $R^5$'s the number of which is n.

11. The anti-tumor composition according to claim 10, wherein the dose ratio of the diaminocyclohexane platinum (II) coordinate complex to the cisplatin coordinate complex is within a range between 1/3 and 3/1, based on the platinum weight.

* * * * *